United States Patent [19]

Castellini

[11] Patent Number: 4,938,692
[45] Date of Patent: Jul. 3, 1990

[54] INSTRUMENT HANDGRIP WITH A BUILT-IN LIGHT

[75] Inventor: Franco Castellini, Bologna, Italy

[73] Assignee: Castellini S.p.A., Bologna, Italy

[21] Appl. No.: 161,447

[22] Filed: Feb. 18, 1988

[30] Foreign Application Priority Data

Feb. 27, 1987 [IT] Italy .................................. 4779/87[U]

[51] Int. Cl.⁵ ............................. A61C 1/00; A61C 3/00
[52] U.S. Cl. ........................................................ 433/29
[58] Field of Search ............................................ 433/29

[56] References Cited

U.S. PATENT DOCUMENTS 4,375,964  3/1983  Knopp et al. ......................... 433/29

Primary Examiner—Robert Peshock
Attorney, Agent, or Firm—Laff, Whitesel, Conte & Saret

[57] ABSTRACT

The removable section of the handgrip is formed with an axial chamber designed to accommodate a lampholder which incorporates a circumferential groove and is seated against a spring that ejects it from the chamber; the spring is kept loaded by a retaining mechanism which locates in the groove, and the entire retaining mechanism is concealed by at least one tubular element that ensheaths the removable section and can be separated from it.

4 Claims, 2 Drawing Sheets

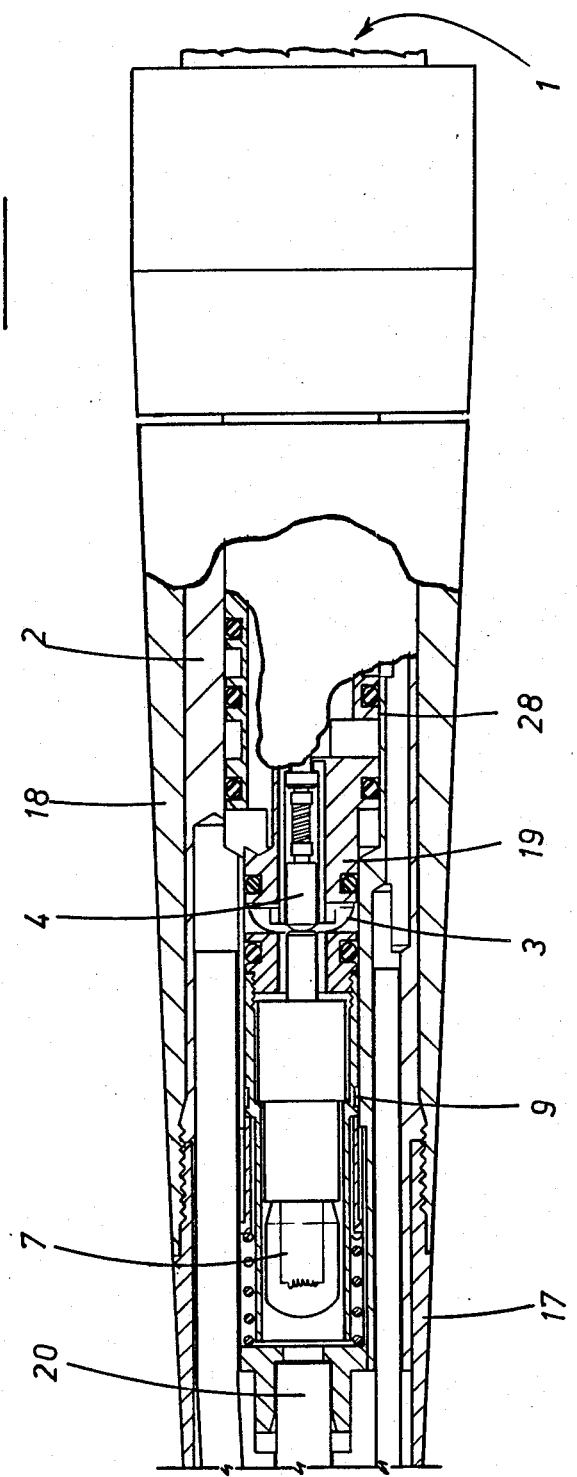

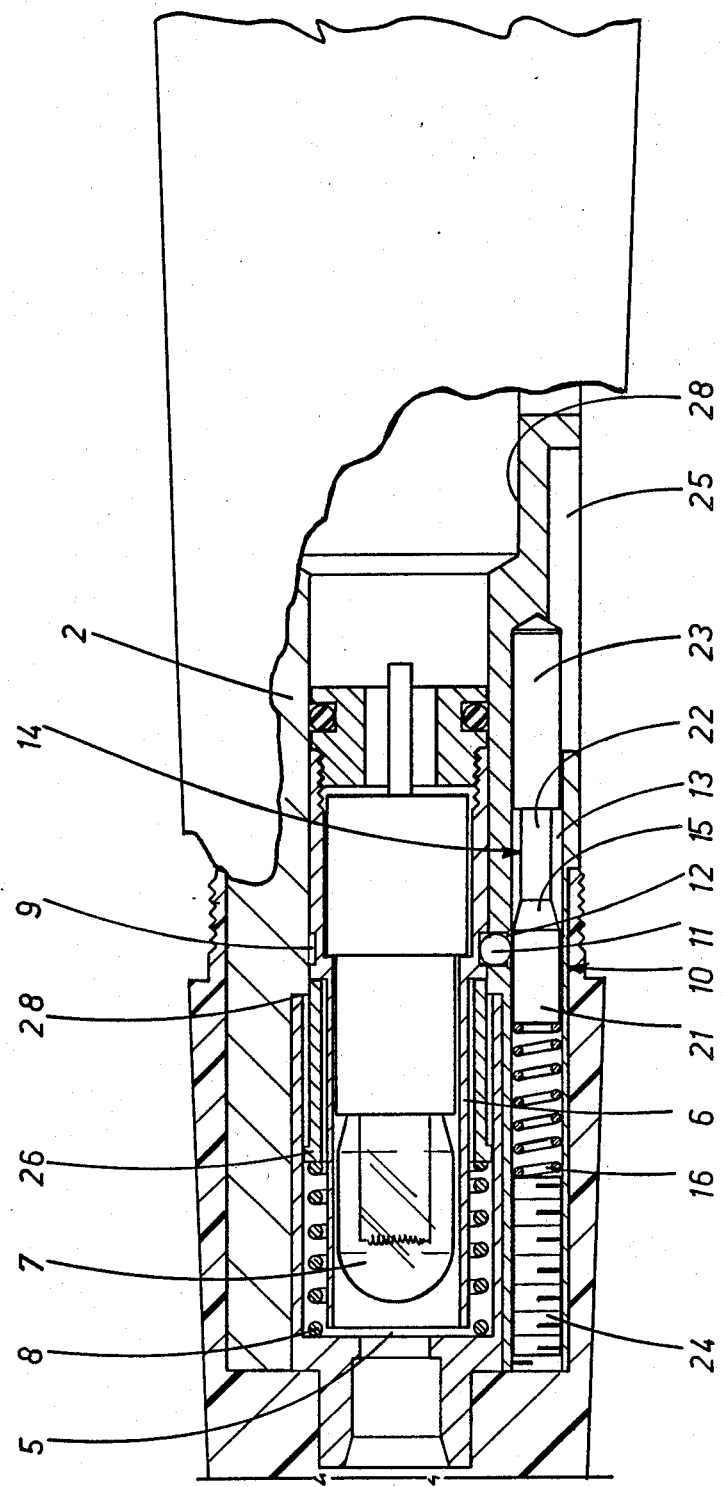

INSTRUMENT HANDGRIP WITH A BUILT-IN LIGHT

BACKGROUND OF THE INVENTION

The invention relates to an instrument handgrip with a built-in light.

The prior art embraces handgrips for dental surgery instruments, marketed recently with the end in view of improving operating and hygiene conditions for the dentist and of ensuring that delicate operations can be effected with less risk to the patient; such holders incorporate their own light source and thus dispense with the need for continual repositioning of overhead lamps during sessions of treatment.

Holders of the type are embodied with a cavity that accommodates a small electric lamp, and incorporate optic fibres that extend from the lamp and shed its light over the treatment area.

The problem encountered with such handgrips is that particularly small lamps must be utilized in order to keep the diametral dimensions compact; also, electric lamps of this size have a relatively short life in view of the output demanded of them, with the result that frequent replacement tends to become necessary.

In a first type of embodiment, the handgrip is split into two discrete sections, one of which fixed permanently to the power supply cable; the remaining section is fastened to and removable from the first, and carries an implement at its projecting end; the electric lamp is accommodated in an axial position by the fixed section, and the removable section is fitted with optic fibres that depart from the center of the end offered to the fixed section.

This type of handgrip enables the electric lamp to be replaced quickly and without difficulty, but is beset by a not insignificant drawback, that is, the lamp remains fully exposed when the sections are separated, and can therefore break somewhat easily.

In a second type of embodiment, similarly split into two sections, one fixed and one removable, the lamp is fitted to the removable section and wired to the fixed section by way of a pair of sliding contacts; in this second embodiment, the removable section is provided with a slot that permits of withdrawing a cover from the recess in which the lamp is housed.

The lamp is better protected here than in the first type mentioned, though hygiene is compromised by the presence of the slot, and moreover, removal of the electric lamp is rendered somewhat difficult both by its own fragility and by the compactness of the handgrip as a whole.

Accordingly, the object of the invention is that of structuring a handgrip of the type in question, that will remain free of the drawbacks mentioned above.

SUMMARY OF THE INVENTION

The stated object is achieved with a handgrip as disclosed and claimed herein.

The difficulties aforementioned are overcome in a handgrip according to the invention by adopting a removable section with an axial chamber, open at the end associating with the fixed section, inside of which a lampholder is accommodated and held, against the action of spring means tending to eject it from the chamber, by retention means designed to engage positively in a circumferential groove offered by the lampholder itself.

One advantage of the invention is essentially that of functional and practical use; to release the electric lamp, it suffices simply to manipulate the retention means in such a way as to trigger the ejection of the lampholder by the spring means.

Another advantage of the invention is that of the degree of hygiene which is obtainable, thanks to the presence of at least one tubular element that ensheaths the entire removable section and ensures that there are no slots, openings or similar points of access in which germs, dust or other hygieneinhibiting agents can collect.

BRIEF DESCRIPTION OF THE DRAWINGS

The invention will now be described in detail, by way of example, with the aid of the accompanying drawings, in which:

FIG. 1 is an axial section through the handgrip as disclosed, viewed with certain parts omitted for the sake of simplicity;

FIG. 2 is an axial section similar to that of FIG. 1, showing the removable section rotated about the axis of the handgrip.

DESCRIPTION OF THE PREFERRED EMBODIMENTS

Referring to FIG. 1, a handgrip according to the invention separates into a fixed section, denoted 1, attached permanently to the end of a cable supplying power to the instrument from a remote source (not illustrated) and a removable section, denoted 2, that attaches coaxially to the free end of the fixed section 1.

The end of the fixed section 1 connecting with the removable section 2 is cylindrical, and exhibits a plurality of circumferential grooves in which to seat respective seals G; the same end also exhibits a cylindrical projection 19 of smaller diameter, likewise embodied with a circumferential groove in which to seat a relative seal G1.

The end of the removable section 2 connecting with the fixed section 1 affords a chamber 28, the shape of which is matched exactly to the end of the fixed section 1 so that the two fit faultlessly together.

The handgrip also comprises ducts, routed into the fixed and removable sections 1 and 2 between each two successive seals, through which water, air etc. are supplied; the ducts are not numbered, being conventional in embodiment.

3 and 4 denote two coaxial sprung contacts which are attached to the end of the projection 19 and directed toward the removable section 2 (see FIG. 1).

20 denotes means, for example, a bundle of optic fibres, that extend through at least a part of the removable section 2 and serv to shed the light from the lamp on the tip of the implement (see FIG. 1).

According to the invention, the end of the removable section 2 connected to the fixed section 1, and in particular, the part extending forward from the chamber 28, incorporates an axial chamber 5 occupied by a lampholder 6, and a relative electric lamp 7. It will be seen that one end of the bundle of optic fibres 20 emerges into the end of axial chamber 5 occupied by the lamp 7. With the handgrip assembled (FIG. 1), the poles 71 and 72 of the lamp 7 connect directly, or indirectly via the lampholder 6, with the contacts 3 and 4 of the fixed section 1 (FIG. 1).

9 denotes a circumferential groove formed in the lampholder 6, which is engaged by retention means 10 that serve to offset the action of a spring 8 loaded between the lampholder 6 and the forward end of the axial chamber 5 (see FIG. 2); more precisely, the retention means 10 prevent the lampholder 6 from leaving the axial chamber 5 under the force of the spring 8 when the removable section 2 is separated from the fixed section 1.

The removable section 2 of the grip is ensheathed by at least one tubular element 18, or in a preferred embodiment, by two such tubular elements 17 and 18 (as in FIG. 1) that can be joined and separated, say, by screw threads.

The forwardmost element 17 -i.e., that nearest to the implement, is integral with the removable section 2, whereas the rear element 18 can be joined to and separated from the other element 17 adopting either a screw fit or a quick-release connection.

The retention means IO consist in a sliding ball 11, and a corresponding radial seat 12 created in the body of the removable section 2. The radial seat 12 extends from the axial chamber 5 and emerges into a longitudinal seat 13, likewise in the body of the removable section 2, that serves to accommodate a spool 14. The depth of the radial seat 12 is less than the diameter of the ball 11, so that part of the ball must necessarily occupy either the axial chamber 5 or the longitudinal seat 13.

The spool 14 exhibits at least three stretches, two of which are cylindrical, denoted 21 and 22, and of dissimilar diameter, located on either side of and interconnected by the third stretch, a conical land denoted 15. The stretch of larger diameter, 21, slides internally of the longitudinal seat 13 with a small margin of clearance. The remaining end of the smaller diameter stretch 22 connects with a further stretch 23 of diameter substantially equal to that of the stretch denoted 21, and serves to guide the movement of the spool internally of the longitudinal seat 13, for reasons that will ultimately become evident.

16 denotes a spring, located between the larger diameter stretch 21 of the spool 14 and one end of the longitudinal seat 13, which serves to bias the spool toward the opposite end of the longitudinal seat 13 (toward the right, in FIG. 2).

The longitudinal seat 13 is stopped by a plug 24 at the end occupied by the spring 16, and opens out radially into a recess 25, created in the removable section 2 and occupied by a part of the spool 14 -viz, part of the stretch denoted 23 (see FIG. 2). The recess 25 is of dimensions such as will afford easy access, for example, to a finger of one hand, so as to permit of urging the spool axially against the action of the spring 16, in the direction of the arrow F1. The recess 25 is encompassed completely by the tubular element denoted 18.

FIG. 2 shows the at-rest position of the spool 14 —i.e. biased toward the right by the spring 16, with its larger diameter stretch 21 positioned alongside the radial seat 12 and preventing the ball 11 from entering the longitudinal seat 13.

26 denotes a sleeve positioned between the lampholder 6 and its spring 8, which slides internally of the axial chamber 5 with a small margin of clearance and is urged into abutment, by the spring 8, against a shoulder 27 offered by the axial chamber 5 itself. The position of the shoulder 27 and the length of the sleeve 26 ensure that when the sleeve registers with the shoulder 27, it will blank off the radial seat 12 and prevent the ball 11 from entering the axial chamber 5.

In a handgrip thus embodied, the fixed and removable sections 1 and 2 combine to create an outer casing that is substantially smooth, and at all events free of slots, recesses etc.

The removable section 2 can be replaced with ease, simply by releasing the fasteners (not shown, being prior art) by which it attaches to the fixed section 1. Separated thus, the fixed section 1 will expose nothing other than the two contacts 3 and 4. The removable section 2, on the other hand, presents a smooth exterior, and the lamp 7 remains safely in position, prevented from leaving the axial chamber by the ball 11, which engages in the circumferential groove 9 of the lampholder 6; more exactly, the ball remains locked in position by the spool 14, biased into the at-rest position of FIG. 2 by its spring 16.

In the event of replacing the electric lamp 7, the removable section 2 is separated from the fixed section 1 and the rear tubular element 18 dismantled in order to expose the recess 25. Inserting a finger or thumb in the recess 25, the user pushes the spool 14 forward, compressing the spring 16 and bringing its smaller diameter stretch 22 into alignment with the radial seat 12. No longer prevented from entering the longitudinal seat 13, and under pressure from the spring 8 impinging on the sleeve 26, the ball 11 shifts from the position of FIG. 2 in the direction of the longitudinal seat 13, and into contact with the smaller diameter stretch 22 of the spool, or with the sloping land 15.

In this situation, the lampholder 6 is subject to no other influence than that of the spring 8, and is duly ejected from the axial chamber 5. In ejecting the lampholder 6, the spring 8 urges the sleeve 26 into contact with the shoulder 27, in such a way that the radial seat 12 is blocked, and the ball 11 prevented from shifting back into the axial chamber 5 under the force of the spring 16 impinging on the spool 14. At this juncture, the dismantled tubular element 18 can be refitted to the other element 17, covering the removable section 2 to ensure maximum possible hygiene.

Once a replacement lamp 7 has been fitted to the lampholder 6, the holder is replaced in the axial chamber 5, and the removable section 1 reconnected with the fixed section 1; the projection 19 of the fixed section 1 now urges the lampholder 6 into the axial chamber 5 against the sleeve 26 and compresses the spring 8.

With the removable section 2 reconnected to the fixed section 1, the circumferential groove 9 of the lampholder 6 aligns with the radial seat 12, and the ball 11 is able to shift away from the longitudinal seat 13 toward the lampholder 6, displaced gradually by the conical land 15 of the spool under pressure from the spring 16; the ball lodges ultimately in the circumferential groove 9 of the lampholder 6, and is retained thus by the large diameter stretch 21 of the spool, now positioned alongside the radial seat 12 as in FIG. 2.

The embodiment of the retaining means 10 might be different to that illustrated; for example, the lampholder 6 could be provided with a longitudinal groove to prevent it from rotating internally of the axial chamber 5, in which case the spool would move tangentially within the removable section 2 and incorporate a projection, shifting internally of the circumferential groove 9 of the lampholder 6 between positions of alignment and non-alignment with the longitudinal groove.

What is claimed:

1. An instrument handgrip with a built-in light, comprising:
   a fixed section, embodied with a projecting axial end provided with a pair of centrally located coaxial electrical contacts;
   a removable section, rotatable and coaxially connected by way of quick-release means to said projecting end of the fixed section, said removable section being provided with an axial backopen chamber open at one end to receive said fixed section and having at its other end a light guiding means;
   a lampholder having a circumferentially groove and housed into said axial chamber, said lampholder having a lamp and poles able to contact directly or indirectly said coaxial electrical contacts;
   a tubular element ensheathing a portion of the removable section incorporating the axial chamber, said tubular element being removable joined to a part of the removable section;
   spring means, positioned between the lampholder and the axial chamber to eject the lampholder from the chamber; and a movable retention means for engaging said circumferential groove of the lampholder and serving to offset the action of the spring means.

2. A handgrip as in claim 1, wherein retention means comprise:
   a ball slidably accommodated in a radial seat, created in the body of the removable section, which is of depth less than the diameter of the ball and extends from the a ial chamber toward a longitudinal seat;
   a spool, accommodated by the longitudinal seat, that exhibits at least one tapered land interconnecting a larger diameter stretch and a smaller diameter stretch, accommodated slidably by the longitudinal seat with a small margin and a generous margin of clearance, respectively, and is capable of movement, controlled by relative spring means, between an atrest position in which the radial seat is adjoined by the larger diameter stretch, and an operative position in which the radial seat is adjoined by the smaller diameter stretch and the ball is able to shift toward the longitudinal seat under the force of the spring means associated with the lampholder; and wherein the longitudinal seat opens outward radially at the end of the spool opposite that which is impinged upon by the spring means, and emerges into a recess, formed in the removable section, which affords access to the longitudinal seat and is encompassed by the tubular element.

3. A handgrip as in claim 2, wherein the axial chamber accommodates a sleeve, positioned between the lampholder and the respective spring means and slidable therein with a small margin of clearance, which is urged by the spring means into contact with a shoulder offered by the axial chamber, and lies alongside the radial seat when thus urged into contact with the shoulder.

4. A handgrip as in claim 1, wherein the axial chamber is embodied with a prominence that locates in a longitudinal groove formed in the lampholder, and retention means consist in a spool, associated with the removable section, which exhibits a projection insertable in the circumferential groove of the lampholder and shifts tangentially between two limit positions in which the projection is moved respectively into and out of alignment with the longitudinal groove of the lampholder.

* * * * *